(12) United States Patent
Cherian et al.

(10) Patent No.: US 8,650,953 B2
(45) Date of Patent: Feb. 18, 2014

(54) CHEMICAL SENSOR WITH REPLACEABLE SAMPLE COLLECTION CHIP

(75) Inventors: Suman Cherian, Singapore (SG); Olivier Le Neel, Singapore (SG)

(73) Assignee: STMicroelectronics Pte Ltd., Singapore (SG)

( * ) Notice: Subject to any disclaimer, the term of this patent is extended or adjusted under 35 U.S.C. 154(b) by 81 days.

(21) Appl. No.: 13/285,867

(22) Filed: Oct. 31, 2011

(65) Prior Publication Data
US 2012/0171774 A1 Jul. 5, 2012

Related U.S. Application Data

(60) Provisional application No. 61/428,826, filed on Dec. 30, 2010.

(51) Int. Cl.
*G01N 7/00* (2006.01)
(52) U.S. Cl.
USPC ......................................... 73/432.1; 73/866.1
(58) Field of Classification Search
USPC .......... 436/95, 94, 93, 91; 257/414; 73/432.1, 73/866.1
See application file for complete search history.

(56) References Cited

U.S. PATENT DOCUMENTS

| | | | |
|---|---|---|---|
| 5,018,395 A | 5/1991 | Hickox et al. | |
| 6,085,576 A | 7/2000 | Sunshine et al. | |
| 6,448,695 B2 | 9/2002 | Milsom | |
| 6,467,332 B1 | 10/2002 | Bertschi et al. | |
| 6,649,357 B2 * | 11/2003 | Bryan et al. | 506/9 |
| 6,821,729 B2 * | 11/2004 | Ackley et al. | 435/6.11 |
| 6,933,807 B2 | 8/2005 | Marksteiner et al. | |
| 7,071,073 B2 | 7/2006 | Villa et al. | |
| 7,294,536 B2 | 11/2007 | Villa et al. | |
| 7,364,896 B2 * | 4/2008 | Schembri | 435/287.1 |
| 7,651,868 B2 * | 1/2010 | McDevitt et al. | 436/518 |
| 2003/0062807 A1 | 4/2003 | Takeuchi et al. | |

(Continued)

FOREIGN PATENT DOCUMENTS

| | | |
|---|---|---|
| EP | 0 822 579 A1 | 2/1998 |
| EP | 1 324 382 A1 | 7/2003 |
| EP | 1 403 383 A1 | 3/2004 |

OTHER PUBLICATIONS

Benetti et al., "Chemical Sensor Based on Thin Film Bulk Acoustic Wave Resonator (TFBAR)," Proceedings of the 10th Italian Conference on Sensors and Microsystems, Firenze, Italy, pp. 326-331, Feb. 15-17, 2005.

(Continued)

*Primary Examiner* — Hezron E Williams
*Assistant Examiner* — Rodney T Frank
(74) *Attorney, Agent, or Firm* — Seed IP Law Group PLLC (57) ABSTRACT

A chemical sensor is provided on a first semiconductor die. A potentiostat is provided on a second semiconductor die. An analog to digital converter and a microcontroller are provided on a third semiconductor die. The first die is configured to be connected to the second die. The second die is configured to be connected to the third die. The chemical sensor detects a chemical in the surrounding environment and outputs a signal to the analog to digital converter. The analog to digital converter converts the signal to a digital signal and outputs the digital signal to the microcontroller. The microcontroller provides a measurement of the concentration of the chemical in the surrounding environment.

13 Claims, 8 Drawing Sheets

(56) References Cited

U.S. PATENT DOCUMENTS

| | | |
|---|---|---|
| 2004/0172798 A1 | 9/2004 | Ruby et al. |
| 2005/0208696 A1 | 9/2005 | Villa et al. |
| 2006/0125489 A1 | 6/2006 | Feucht et al. |
| 2006/0257286 A1 | 11/2006 | Adams |
| 2010/0107739 A1 | 5/2010 | Marra |
| 2010/0163410 A1 | 7/2010 | Mastromatteo et al. |
| 2010/0170324 A1 | 7/2010 | Mastromatteo et al. |
| 2011/0209524 A1 | 9/2011 | Ziglioli et al. |
| 2011/0318840 A1 | 12/2011 | Ziglioli et al. |
| 2012/0168882 A1* | 7/2012 | Cherian et al. ............ 257/414 |
| 2012/0171713 A1* | 7/2012 | Cherian et al. ............ 435/29 |

OTHER PUBLICATIONS

D'amico et al., "Olfactometric Apparatus Based on Oscillating Crystal Sensors Functionalised with Tetrapyrrolic Macrocycles and Provided with Electronics for Conditioning and Reading the Signals, Communicating with a PC, Managing Through a Software and Analysis and Displaying the Data," Italian Patent Application No. RM2001A000455, filed Jul. 26, 2001, 20 pages w/English translation.

Matsumoto et al., "Influence of Underlayer Materials on Preferred Orientations of Sputter-Deposited AIN/MO Bilayers for Film Bulk Acoustic Wave Resonators," *Japanese Journal of Applied Physics* 43(12):8219-8222, 2004.

Richter et al., "A High Performance Silicon Micropump for Fuel Handling in DMFC Systems," proceedings of the Fuel Cell Seminar, Miami Beach, FL, USA, pp. 272-275, Nov. 3-7, 2003.

Rosenbaum, "Bulk Acoustic Wave Theory and Devices," Boston, MA: Artech House, 1988, 7 pages.

Cherian et al "Single Chip Having the Chemical Sensor and Electronics on the Same Die," U.S. Appl. No. 13/285,894, filed Oct. 31, 2011, 35 pages.

Cherian et al., "Integrated Chemical Sensor," U.S. Appl. No. 13/285,911, filed Oct. 31, 2011, 56 pages.

Hwang et al., "CMOS VLSI Potentiostat for Portable Environmental Sensing Applications," *IEEE Sensors Journal* 10 (4):820-821, Apr. 2010.

Schienle et al., "A Fully Electronic DNA Sensor With 128 Positions and In-Pixel A/D Conversion," *IEEE Journal of Solid-State Circuits* 39(12):2438-2445, Dec. 2004.

Turner et al., "A CMOS Potentiostat for Amperometric Chemical Sensors," *IEEE Journal of Solid-State Circuits*, SC-22(3):473-478, Jun. 1987.

Yang et al., "Amperometric Electrochemical Microsystem for a Miniaturized Protein Biosensor Array," *IEEE Transactions on Biomedical Circuits and Systems* 3(3):160-168, Jun. 2009.

Zhang et al., "Electrochemical Array Microsystem with Integrated Potentiostat," *IEEE Sensors*, pp. 385-388, 2005.

* cited by examiner

CHEMICAL SENSOR WITH REPLACEABLE SAMPLE COLLECTION CHIP

CROSS-REFERENCE TO RELATED APPLICATION

This application claims the benefit under 35 U.S.C. §119 (e) of U.S. Provisional Patent Application No. 61/428,826 filed Dec. 30, 2010 and is incorporated herein by reference in its entirety.

BACKGROUND

1. Technical Field

The present disclosure relates to a chemical sensor formed in a semiconductor die.

2. Description of the Related Art

Chemical sensors are used in a variety of applications. Chemical sensors are used in medical applications, industrial applications, automotive applications, security applications, and domestic applications. Some examples of chemical sensors are blood glucose sensors, carbon dioxide detectors, automobile exhaust emission monitors, radon detectors, carbon monoxide detectors, explosives detectors, and a large variety of other applications.

In the past, many chemical sensors have been large and relatively expensive. Some chemical sensors are used in applications in which they may only be used a single time. Such single use sensors are typically used in biomedical applications. It can be very expensive to replace an entire chemical detection system after each use. It may thus greatly increase the cost of medical diagnosis and treatment.

BRIEF SUMMARY

One embodiment is chemical detection system including three semiconductor dies. A chemical sensing portion of the system is formed on a first replaceable semiconductor die. The chemical sensing portion outputs an analog signal indicative of the presence of the chemical to be detected. The system further includes an analog to digital converter formed in a second semiconductor die. The analog to digital converter receives the analog signal and converts it to a digital signal. The system further includes a microcontroller formed in a third semiconductor die. The microcontroller receives the digital signal from the analog to digital converter and calculates the concentration of the chemical to be detected.

The chemical sensor is formed on a semiconductor die separate from the analog to digital converter and the microcontroller. When the chemical sensor is installed in the system the first semiconductor die is electrically connected to the digital to the second semiconductor die, including the digital to analog converter. After the chemical sensor has been used, the first semiconductor die including the chemical sensor is removed from the system. The first semiconductor die is then replaced by another semiconductor die including a chemical sensor. The system is then prepared for a second use.

Fabrication of CMOS analog to digital converters and complex microcontrollers can be very costly. Because the analog to digital converter and the microcontroller are formed on dice separate from the die including the chemical sensor, the first semiconductor die including the chemical sensor can be fabricated relatively inexpensively.

In one embodiment a signal amplifier is formed in the second semiconductor die with the analog to digital converter. The signal amplifier amplifies the analog signal from the chemical sensor to enable the analog to digital converter to make a reliable conversion. In one embodiment the signal amplifier is a potentiostat. When the chemical sensor die is installed in the system the potentiostat controls the voltages on sensitive electrodes of the chemical sensor and amplifies a current signal from the chemical sensor. The analog to digital converter then converts the amplified analog signal to a digital signal.

In one embodiment the analog to digital converter and the microcontroller are formed in the same semiconductor die.

In an alternative embodiment the analog to digital converter and the chemical sensor are formed in the same semiconductor die.

DETAILED DESCRIPTION

Figure 1:
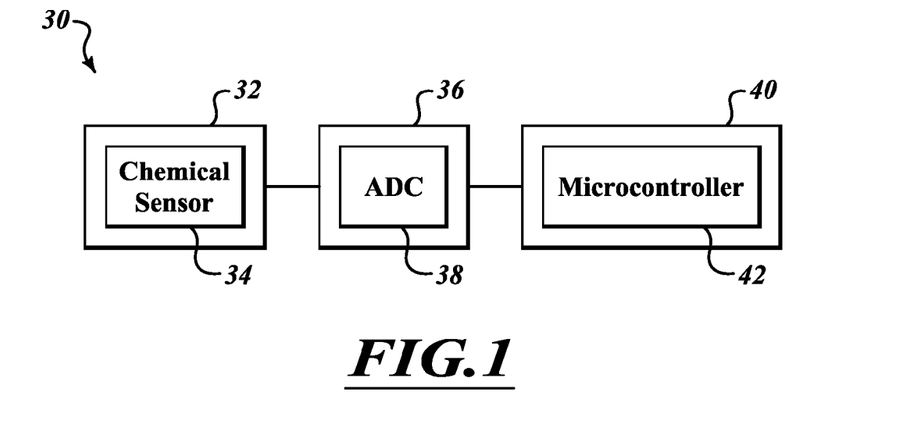
FIG. 1 is a block diagram of a chemical sensing system according to one embodiment.

FIG. 1 illustrates a chemical detection system 30. The system 30 includes a first semiconductor die 32. A chemical sensor 34 is formed in the first semiconductor die 32. The first semiconductor die 32 is electrically coupled to a second semiconductor die 36. An analog to digital converter is formed in the second semiconductor die 36. The second semiconductor die 36 is electrically coupled to a third semiconductor die 40. A microcontroller 42 is formed in the third semiconductor die 40.

The chemical sensor 34 is configured to sense the presence of a selected chemical. The chemical sensor 34 can be manufactured to detect one or more of a variety of chemicals. For medical applications the chemical sensor 34 can be designed to detect glucose in blood, cholesterol in blood, hemoglobin, various gasses in blood, cancer markers, the presence of electrolytes, blood urea nitrogen (BUN), drugs in the blood stream, DNA, RNA, and myriad other possible chemicals or compounds. For industrial applications the chemical sensor 34 can be designed to detect pH levels, Pb, Hg, Cr, Cd, As Sb, Be, fluorides, volatile organic compounds (VOCs), etc. The chemical sensor 34 can be designed for environmental applications such as detecting CO, NOx, Ra, H2S, HCN, CO2, air, water, CN, microorganisms, etc. For automotive applications the chemical sensor 34 can be configured to detect many kinds of pollutants in the exhaust of an automobile, such pollutants can include CO, NOx, O, and other particulates. The chemical sensor 34 may detect just one chemical or it may have multiple sensors adjacent each other on the same die to sense dozens of different chemicals with a single sensor.

The chemical sensor 34 outputs an analog signal to the analog to digital converter 38 in the second semiconductor die 36. The analog signal is indicative of the presence of the selected chemical to be detected. In one embodiment the analog signal varies according to the concentration of the selected chemical in the vicinity of the chemical sensor 34. The analog to digital converter 38 converts the analog signal to a digital signal. The analog to digital converter 38 then outputs the digital signal to the microcontroller 42 in the third semiconductor die 40. The microcontroller 42 receives the digital signal and computes a value of the concentration of the chemical in the vicinity of the chemical sensor 34.

In one embodiment the microcontroller 42 stores a plurality of possible digital signal data values in memory, each data value being correlated to a respective value of the concentration of the selected chemical in the vicinity of the chemical sensor 34. When the microcontroller 42 receives the digital signal from the analog to digital converter 38, the microcontroller 42 compares the digital signal to the digital signal values stored in memory and estimates the concentration of the selected chemical according to the concentration values stored in memory.

In one embodiment the microcontroller 42 computes the value of the concentration of the selected chemical based on the digital signal and other data representative of environmental conditions. For example, the analog signal output by the chemical sensor 34 can be influenced by the temperature or the humidity of the surrounding environment. The microcontroller 42 may receive temperature or humidity data in addition to the digital signal. The microcontroller 42 may then take into account the humidity and temperature data when computing the value of the concentration of the selected chemical. The humidity and temperature data may be supplied by a humidity sensor and a temperature sensor also located in the first semiconductor die 32.

In one embodiment the system 30 can detect multiple selected chemicals. The first semiconductor die 32 is a replaceable semiconductor die. The semiconductor die 32 can be easily removed from the system 30 and replaced by a first semiconductor die that is configured to sense a different selected chemical. The microcontroller 42 is configured to compute the value of the concentration of a variety of different chemicals. In one embodiment the microcontroller receives an input that identifies the type of chemical sensor 34 that has been placed in the system 30. The input can be received from a user, or from an electronic signature of the first semiconductor die 32. The microcontroller 42 receives the digital signal from the analog to digital converter 38 and computes a value of the concentration according to the input that identifies the selected chemical.

In one embodiment multiple first semiconductor dice 32, each containing a different type of chemical sensor 34, are installed in the system 30. Each die 32 outputs an analog signal to the analog to digital converter 38, or to respective analog to digital converters 38 all on the second semiconductor die 36. The analog to digital converter 38 then outputs digital signals to the microcontroller 42. Each digital signal is a conversion of an analog signal from a respective chemical sensor. The microcontroller 42 computes the values of the concentrations of the respective selected chemicals.

In one embodiment the microcontroller 42 stores a calibration table in memory. The calibration table stored in the microcontroller 42 is specific to the type of chemical sensor 34 formed in the semiconductor die 32. When the microcontroller 42 receives the digital signal from the analog to digital converter 38 the microcontroller 42 compares the digital signal to a calibration table as one step in computing the value of the concentration of the selected chemical. The memory of the microcontroller 42 can be programmed with calibration table according to the selected chemical. The calibration table can be updated or replaced if a more accurate calibration data is been developed. According to another embodiment, a conversion curve or conversion database is stored in the memory of the microcontroller 42. A conversion curve is a simple series of data points in which the value of the analog signal represents the x-axis and the concentration of the chemical of interest represents the y-axis. Thus, when the microcontroller 42 receives the digital data from the analog-to-digital converter 38, a simple comparison to the conversion curve outputs the relative concentration of the selected chemical. For some types of chemical sensing circuits, a conversion curve, sometimes termed a calibration curve, is a preferred tool for assistance in computing the concentration of the selected chemical. In other instances, a full conversion table, a calibration table, is preferred. For example, in many instances, the value of the digital data corresponding to the sensed chemical may be only one of the data points in determining the concentration of the selected chemical. Other ambient conditions may be sensed in order to accurately determine the concentration, such as the humidity, the temperature, the pH of the moisture content, and other factors. Thus, in many instances the conversion table may have different values for the conversion depending on the temperature of the sensor, the humidity of the sensor, and other factors. Thus, the conversion table may include a plurality of separate tables, one for each temperature or temperature range, and again, depending on the selected chemical to be sensed and whether or not the sensing varies according to temperature. There are a number of well-known techniques for converting an analog signal representative of the presence of a selected chemical to a data value indicative of the concentration of that selected chemical.

In one embodiment, the concentration of the chemical is not as important as the presence of the chemical or that the chemical is above a selected threshold. For example, in some embodiments, the mere presence of a particular chemical, such as carbon monoxide, certain types of blood cells, is sufficient to indicate the test is positive as compared to a negative. Accordingly, in some embodiments, the chemical sensor will output a signal indicating that the chemical has been sensed as present, and this alone is sufficient for purposes of the particular product. Thus, in this embodiment, the output signal is whether the selected chemical is present or not present, rather than providing a selected concentration of the particular chemical. In other embodiments, the signal is output if the selected chemical is above a threshold. For example, it may be desired to know whether or not carbon monoxide is above a selected threshold level in a particular environment. In such situations, the sensor will detect the presence of carbon monoxide and if it is determined to be below a selected threshold, then no signal is output. If, on the other hand, the presence of the carbon monoxide is above a selected threshold value, then a separate signal is output, such as an alarm signal, to indicate that the carbon monoxide in the local environment has exceeded a desired level and safety precautions should be taken. Thus, in this embodiment, the chemical sensor integrated with the semiconductor die is a threshold sensor outputting a signal that the chemical is above a selected threshold, rather than providing the exact number of the concentration of that particular chemical. Of course, the microcontroller 42 can compute or estimate the value of the concentration or it if is above a selected threshold of the selected chemical through any number of suitable ways which are equivalent to and interchangeable with each other in light of the present disclosure.

Figure 2:
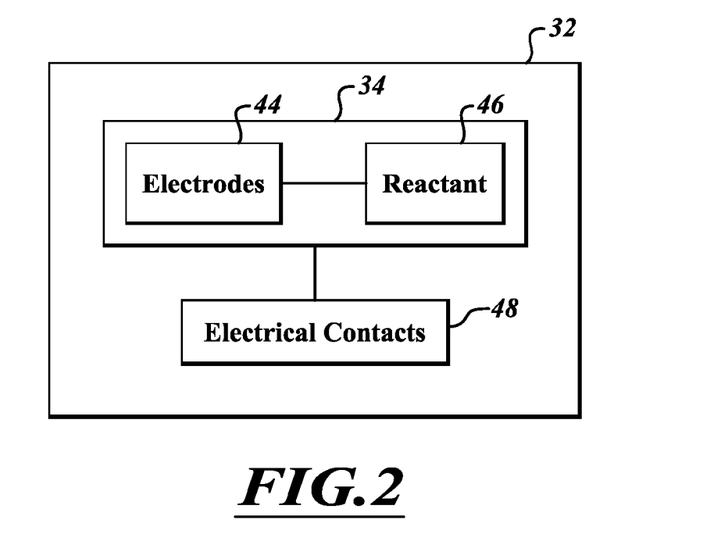
FIG. 2 is a block diagram of a first semiconductor die according to one embodiment.

FIG. 2 illustrates the first semiconductor die 32 according to one embodiment. The first semiconductor die 32 includes a chemical sensor 34. The chemical sensor 34 includes electrodes 44 positioned near the top surface of the first semiconductor die 32. A chemical reactant 46 is positioned adjacent the electrodes 44. The type of chemical reactant 46 depends on the specific application of the chemical sensor 34. The chemical reactant is configured to react with the selected chemical. In one embodiment a voltage is applied to the electrodes 44. The analog signal is a current signal coming from the electrodes 44. The current from the electrodes increases as the selected chemical is incident on the chemical reactant 46. The higher the concentration of the selected chemical, the higher the current signal output from the electrodes 44. In this way the analog current signal is indicative of the concentration of selected chemical in the vicinity of the chemical sensor 34.

In one embodiment the first semiconductor die is covered in a passivation material. During manufacture of the first semiconductor die 32 the passivation material is etched to expose electrodes 44. The electrodes 44 are then covered in the reactant 46. The reactant 46 is therefore exposed to the air or other environment surrounding the first semiconductor die 32. In this way the reactant 46 can react with the concentration of the selected chemical in the vicinity of the first semiconductor die 32. In one embodiment the reactant 46 is an enzyme. The reactant 46 may also be cells, antibodies, DNA/RNA sequences, customized molecules, or any other substance that reacts with or is sensitive to the selected chemical. While the transduction of the chemical reaction generates an electrical current or voltage signal, other types of transduction may be used including optical signals, frequency signals, capacitive signals, or any other suitable signal.

The first semiconductor die 32 also includes electrical contacts 48 coupled to the chemical sensor 44. The electrical contacts 48 allow the first semiconductor die 32 to be electrically connected to the chemical detection system 30, and to the second semiconductor die 36 in particular. The analog to digital converter 48 can receive the analog signal from the chemical sensor 34 through the electrical contacts 48. Electrical contacts 48 can include contact pads, ball grid arrays, pin grid arrays, a lead frame, or many other types of connections as will be apparent to those of skill in the art in light of the present disclosure.

A more detailed description of the specific manufacture of chemical sensors can be found in copending U.S. patent application Ser. Nos. 13/016,086, 13/170,058, and U.S. patent application Ser. Nos. 13/285,894, 13/285,911, all which are incorporated by reference in their entireties.

Figure 3:
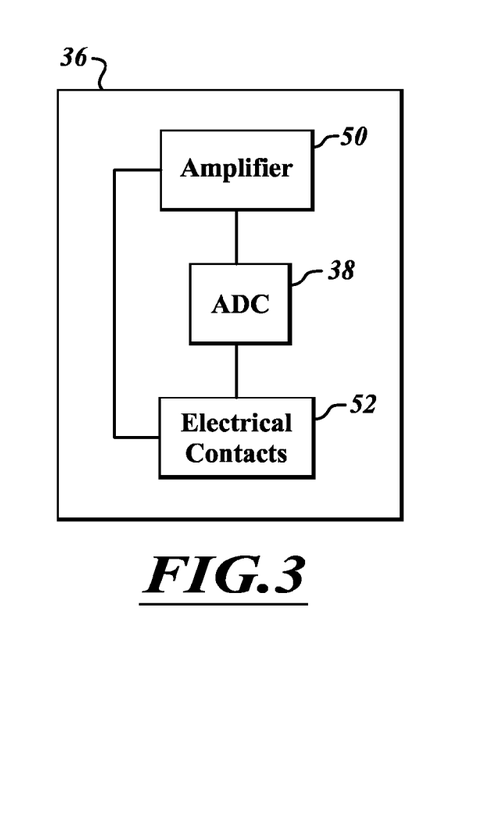
FIG. 3 is a block diagram of a second semiconductor die according to one embodiment.

FIG. 3 illustrates the second semiconductor die 36 according to one embodiment. The second semiconductor die includes an analog to digital converter 38, electrical contacts 52, and an amplifier 54. According to one embodiment the amplifier receives the analog signal from the chemical sensor 34 through electrical contacts 52. In one embodiment the analog signal received from the chemical sensor 34 is a very weak signal. The chemical sensor 34 is located on a separate semiconductor die 32 and there can be signal attenuation between the chemical sensor 34 and the analog to digital converter 38. Furthermore, due to the relatively far distance between the chemical sensor and the analog to digital converter 38, noise can be added to the signal. This can cause the signal to noise ratio of the analog signal at the analog to digital converter 38 to be disadvantageously low. A low signal to noise ratio can cause the analog to digital converter 38 to give an inaccurate conversion of the analog signal to a digital signal. The microcontroller 42 may in turn provide an inaccurate value of the concentration of the selected chemical.

In order to ensure that the analog to digital converter 38 can reliably convert the analog signal to a digital signal, the amplifier 50 first amplifies the analog signal. The amplifier 50 then provides an amplified analog signal to the analog to digital converter 38. In this way the analog to digital converter 38 can provide an accurate conversion of the analog signal to a digital signal.

Electrical contacts 52 allow electrical connections between the first semiconductor die 32 and the second semiconductor die 36. This allows the chemical sensor 34 to provide the analog signal to the amplifier 50. In one embodiment the amplifier 50 also applies a constant voltage to the electrodes 44 of the chemical sensor 34. The amplifier 50 thus acts a control circuit for the chemical sensor 34. As the amplifier 50 applies a constant voltage to the electrodes 44, the amplifier 50 also receives and amplifies an analog current signal received from the electrodes 44.

In one embodiment the amplifier 50 is a potentiostat having both a control portion and an amplification portion. The control portion of the potentiostat controls the voltage between the electrodes 44. The amplification part of the amplifier 50 receives the analog current signal and converts it to an analog voltage signal. The amplifier 50 then supplies the analog voltage signal to the analog to digital converter 28.

The amplifier 50 can be an amplifier other than a potentiostat. The amplifier 50 can be implemented in many other kinds of circuits as will be apparent to those of skill in the art in light of the present disclosure.

Electrical contacts 52 also electrically connect the analog to digital converter 38 to the microcontroller 42 of the third semiconductor die 40. The analog to digital converter 38 outputs the digital signal to the microcontroller 42 through electrical contacts 52. Electrical contacts 52 can include contact pads, ball grid arrays, pin grid arrays, leads of a lead frame, or many other types of connections as will be apparent to those of skill in the art in light of the present disclosure.

Figure 4:
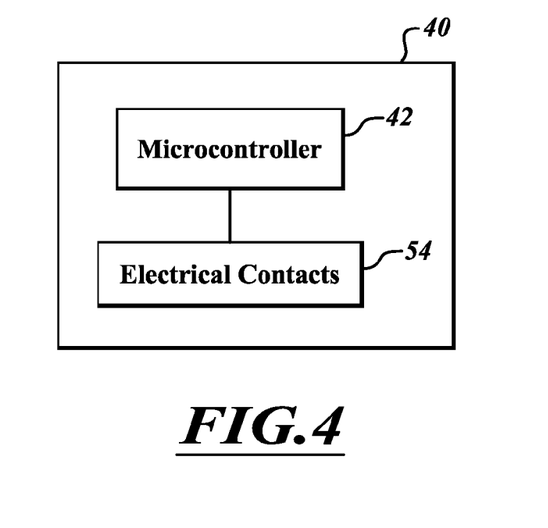
FIG. 4 is a block diagram of a third semiconductor die according to one embodiment.

FIG. 4 illustrates the third semiconductor die 40. The semiconductor die 40 includes microcontroller 42 and electrical contacts 55. The analog to digital converter 38 of the second semiconductor die 36 outputs the digital signal to the microcontroller 42 in the third semiconductor die 40. The microcontroller 42 receives the digital signal and computes a value of the concentration of the chemical in the vicinity of the chemical sensor 34.

The microcontroller is electrically connected to the analog to digital converter 38 by electrical contacts 55. Electrical contacts 55 can include contact pads, ball grid arrays, pin grid arrays, leads of a lead frame, or many other types of connections as will be apparent to those of skill in the art in light of the present disclosure. The electrical contacts 55 may also connect the third semiconductor die 40 to a power source. The first and second semiconductor dice 32, 36 may receiver power from the third semiconductor die 40 through electrical contacts 48, 52, and 55.

Figure 5:
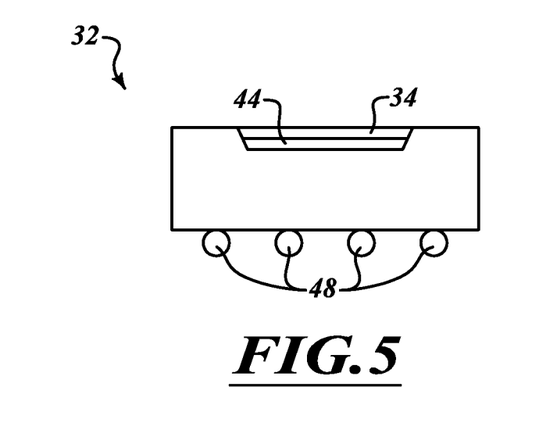
FIG. 5 is a cross section of a first semiconductor die according to one embodiment.

FIG. 5 is a cross section of the first semiconductor die 32. Chemical sensor 34 includes electrode 44 and reactant 46. The reactant 46 is on top of electrode 44. The reactant 46 has been placed on the electrode 44 through an opening etched in molding compound encapsulating the die 32. A top surface of the reactant 46 is exposed to the surrounding environment. When in use control signals may be applied to electrode 44 through electrical connections 48 as described previously. The analog signal from the chemical sensor 34 may be passed to the second semiconductor die 36 through the first electrical connections 48.

The electrical connections 48 are illustrated as solder balls of a ball grid array. Such a ball grid array 48 may be implemented in any suitable way. In one embodiment the ball grid array is an embedded wafer level ball grid array (EWLB). An EWLB allows for easy redistribution of electrical connections from the top of the die 32 to the bottom of the die 32 or vice versa. Other types of electrical connections may also be used such as a lead frame, a pin grid array, wire bonding, or any other suitable structures as will be apparent to those of skill in the art in light of the present disclosure.

Figure 6:
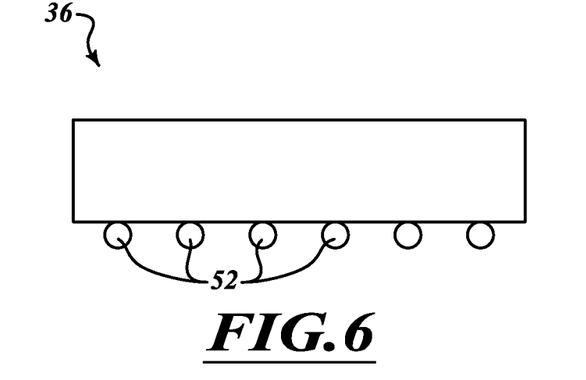
FIG. 6 is a cross section of a second semiconductor die according to one embodiment.
Figure 7:
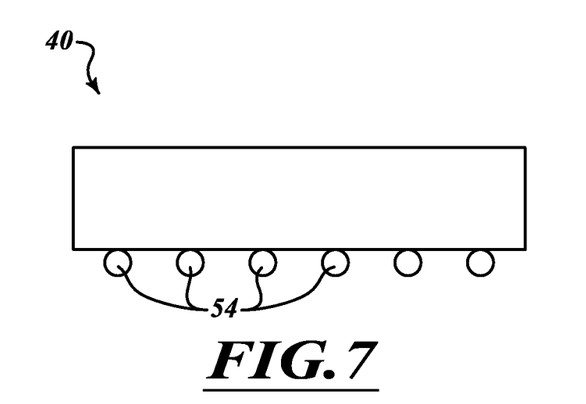
FIG. 7 is a cross section of a third semiconductor die according to one embodiment.

FIGS. 6 and 7 are respective cross sections of the second semiconductor die 36 and the third semiconductor die 40. The internal circuitry such as analog to digital converter 38 and microcontroller 42 are not illustrated. The semiconductor dice 36, 40 are illustrated as packaged die including electrical connections 52 and 54. The electrical connections 52, 54 are illustrated as solder balls of a ball grid array. Such a ball grid array 52, 54 may be implemented in any suitable way. In one embodiment the ball grid array is an embedded wafer level ball grid array (EWLB). An EWLB allows for easy redistribution of electrical connections from the top of the die 36 or 40 to the bottom of the die 36 or 40 or vice versa. Other types of electrical connections may also be used such as a lead frame, a pin grid array, wire bonding, or any other suitable structures as will be apparent to those of skill in the art in light of the present disclosure.

Figure 8:
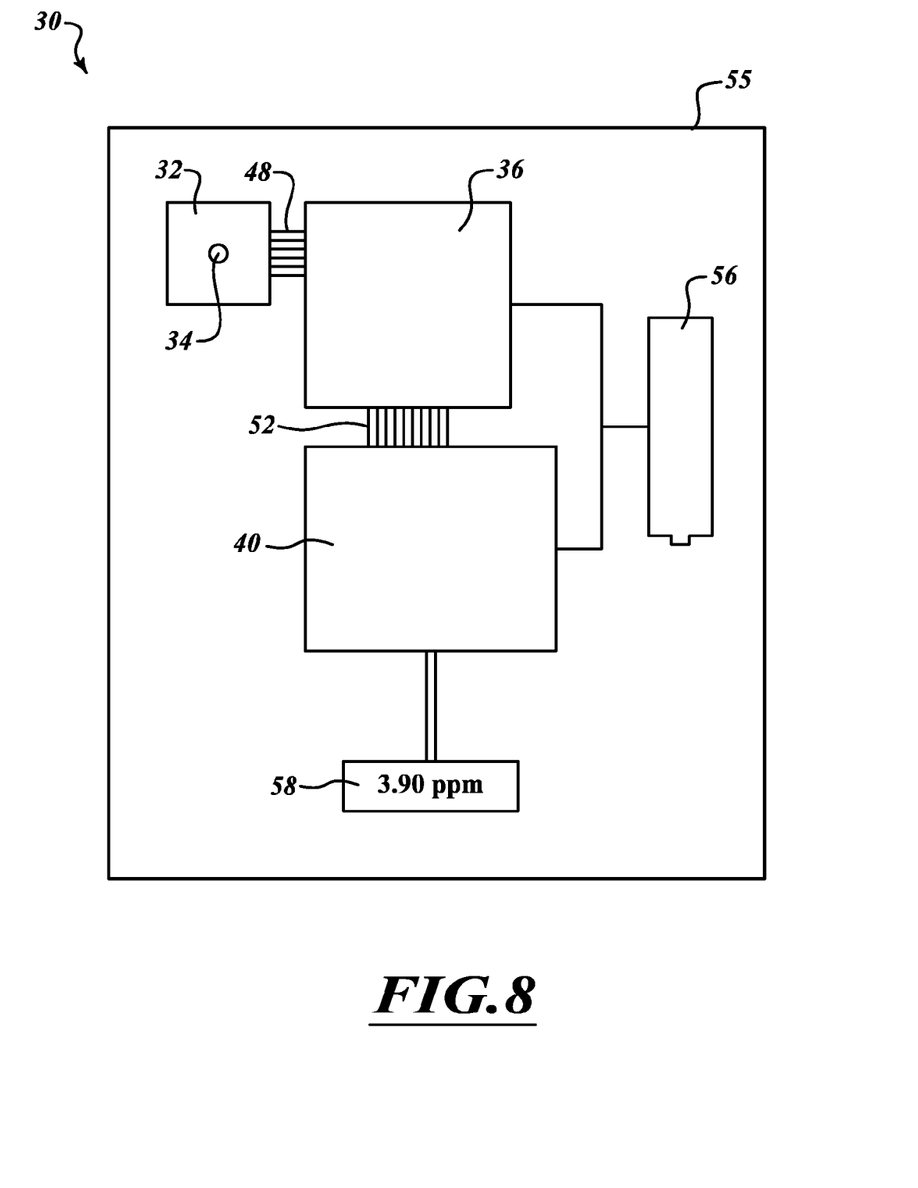
FIG. 8 illustrates a chemical detection system according to one embodiment.

FIG. 8 illustrates a chemical detection system 30 according to one embodiment. The system 30 includes a casing 55. The first, second, and third semiconductor dice 32, 36, 40 are installed in the casing 55. The first semiconductor die 32 is connected to the second semiconductor die 36 by electrical connections 48. In one embodiment the electrical connections 48 connects the first semiconductor die 32 to conductive paths in a printed circuit board. The conductive paths connect the first semiconductor die 32 to the second semiconductor die 36. The second semiconductor die 36 is connected to the third semiconductor die 40 by electrical connections 52. In one embodiment the electrical connections 52 connects the second semiconductor die 36 to conductive paths in a printed circuit board. The conductive paths connect the second semiconductor die 36 to the third semiconductor die 40. Chemical sensor 34 is visible atop the first semiconductor die 34.

A battery 56 is also installed in the casing 55. The battery 56 supplies power to both the second semiconductor die 36 and the third semiconductor die 40. In one embodiment the battery 56 is directly connected to only the third semiconductor die 40. The third semiconductor die then supplies power to the second semiconductor die 36 through electrical connections 52. The second semiconductor die 36 supplies power to the first semiconductor die. In one embodiment the battery 56 supplies power to all three semiconductor dice 32, 36, 40 directly.

The third semiconductor die 40 is connected to a display 58. The microcontroller 42 in the third semiconductor die 40 computes a value of the concentration of the selected chemical and outputs the value to the display 58. The display 58 displays the value concentration of the selected chemical. The display 58 can be a digital display, an LCD screen, a printer that prints the value on paper, or any other suitable means for displaying the value of the concentration.

In one embodiment the system 30 is a blood glucose measuring system. The first semiconductor die 32 is a disposable semiconductor die. To test the blood glucose concentration, a blood sample is placed on the first semiconductor die 32 on the reactant 46 of the chemical sensor 34. The chemical sensor 34, the analog to digital converter 38, the microcontroller 42 may then operate as described above to compute or estimate a value of the concentration of glucose in the blood sample. The display 58 displays the value of the concentration of glucose in the blood.

Thereafter the system 30 may be used to perform another blood glucose test. The casing 55 is designed to allow for easy removal of the replaceable first semiconductor die 32. An identical replacement first semiconductor die 32 is then installed in the casing 55. A second blood sample is placed on the replacement first semiconductor die 32 and the system 30 again outputs a value of the concentration of glucose in the blood. The replacement die 32 has not been contaminated by the first blood test and the system 30 may thus be reused multiple times. With each reuse the first semiconductor die 32 is replaced with a new first semiconductor die 32.

Because the first semiconductor die 32 does not contain the complex circuitry of the microcontroller 42 or even the less complex circuitry of the analog to digital converter 38, the first semiconductor die 32 can be manufactured in a relatively inexpensive manner. Thus a single blood glucose detection system 30 can be reused inexpensively by replacing the first semiconductor die 32 as often as the system 30 is used. While one embodiment of system 30 is a blood glucose measurement system, the system 30 may be designed to detect a variety of other selected chemicals as described in relation to FIG. 1.

In one embodiment the system 30 is designed to detect if the concentration of the selected chemical is above a selected threshold value. If the microcontroller 42 determines that the concentration is above the selected threshold value then the display 58 may simply issue an alert that the threshold has been surpassed. In one embodiment the display 58 is an LED or series of LEDs that displays a first color when the concentration is above the selected threshold. The LED or series of LEDs may display a second color if the concentration of the chemical is below a predicted threshold. In one embodiment the display 58 includes a speaker that emits an audible sound if the concentration of the chemical is above the selected threshold.

While the system 30 of FIG. 8 is described as being housed in a single casing 55, in one embodiment one or more components of the system 30 are outside of the casing 55. In one embodiment the display 58 is outside of the casing 55. The microcontroller 42 may be connected to a display 58 or computer in a separate room or location from the chemical sensor 34. In one embodiment the display 58 is a computer monitor or screen in a different room.

In one embodiment the third semiconductor die 40 is in a separate location from the first and second semiconductor dice 32, 36. The analog to digital converter 38 sends the digital signal to the third semiconductor die 40 in a separate room or location. The microcontroller 42 may then process the digital signal and output a signal to the display 58. The display 58 may be in the vicinity of the first semiconductor die 32 or in a separate like location with the third semiconductor die 40.

Figure 9:
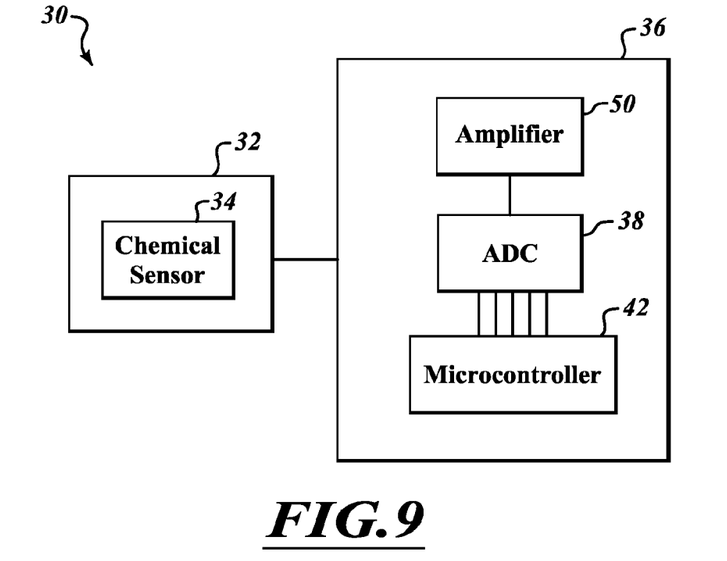
FIG. 9 is a block diagram of a two die chemical detection system according to one embodiment.

FIG. 9 illustrates a chemical detection system 30 according to one embodiment. The analog to digital converter 38, the amplifier 50, and the microcontroller 42 are all formed in the second semiconductor die 36. The chemical sensor 34 is formed in the first semiconductor die 32. The chemical sensor 34 outputs an analog signal to the second semiconductor die 36. The analog signal is amplified by the amplifier 50 and output to the analog to digital converter 38. The analog to digital converter 38 converts the analog signal to a digital signal. The analog to digital converter 38 outputs the digital signal to the microcontroller 42. The microcontroller 42 computes or estimates a value of the concentration of the selected chemical as described above.

The amplification, conversion to digital, and computation of the value are all performed on a single semiconductor die 36. Because the system 30 may be implemented in two dice instead of three semiconductor dice, the expense of manufacturing the system 30 can be reduced.

Figure 10:
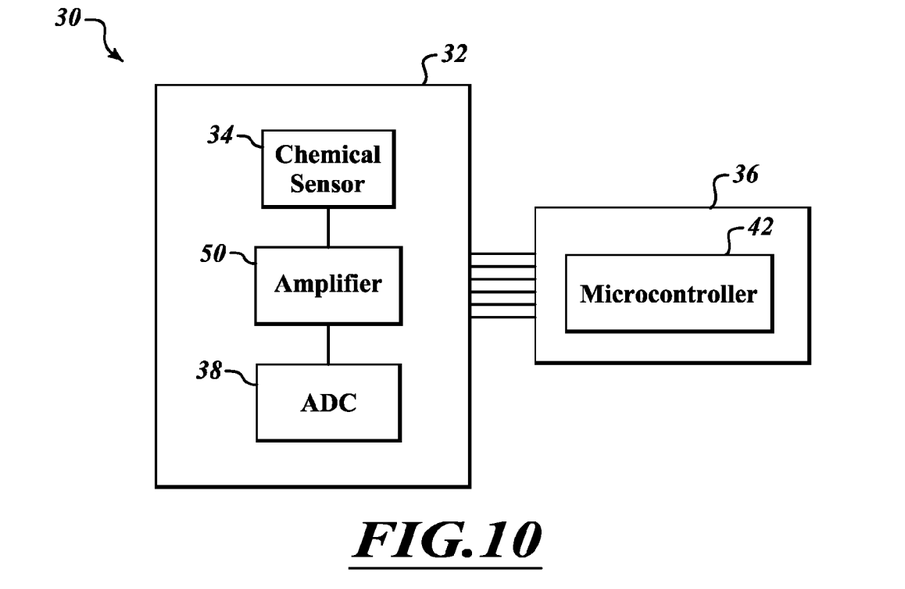
FIG. 10 is a block diagram of a two die chemical detection system according to a further embodiment.

FIG. 10 illustrates a chemical detection system 30 according to one embodiment. The first semiconductor die 32 includes the chemical sensor 34, amplifier 50, and analog to digital converter 38. Each of these components performs substantially similar functions as those described above.

The analog signal output by a chemical sensor 34 may be very weak. If the analog to digital converter 38 is on a separate semiconductor die from the chemical sensor 34, then the analog signal may be greatly attenuated by the time it is received by the analog to digital converter 38. Furthermore, much noise may be introduced into the analog signal if the analog signal is sent from one semiconductor die to another. This causes the signal to noise ratio to decrease and the digital to analog converter 38 may give a relatively inaccurate digital conversion of the original analog signal.

Having the analog to digital converter 38 on the same die as the chemical sensor 34 provides the ability to obtain accurate chemical sensing using very small sample sizes. Once the analog signal has been converted to the digital signal by the analog to digital converter 38, the digital signal is substantially immune to noise. With a digital signal, the data being transmitted is a one or a zero, and therefore greater discrimination can be provided between the signal content and the noise content. Additionally, a digital signal may carry a large number of check bits, parity bits, or other type of error checking bits. In an 8-bit signal, two or three of the bits may be used as error correction code bits so that even if some noise is present in the coupling between the first semiconductor die 32 and the second semiconductor die 36, the microcontroller 42 can check the error correction bits contained in each byte and correct the errors to be assured that the data being received is the data that was sent. The ability to provide a large number of error correction bits across multiple bytes of data is a significant benefit with converting the data to a digital format prior to sending. In addition, the analog-to-digital converter 38 will often have a memory buffer so that the same data can be set in separate groups of bytes, separated from each other in time so that if the first set of bytes is subjected to noise, then a later second set of bytes set at a different time having the same data may avoid the same noise. In addition, repeatedly sending the same data in separate groups of bytes spaced in time permits the microcontroller 42 to compare the various sets of data with each other as part of the error correction code in order to be assured that the correct data has been received by the microcontroller 42. Thus, having an analog-to-digital converter 38 with a small buffer memory, whether it be SRAM registers, shift registers, or other small memories, is beneficial to achieve the purposes of sensing small quantities of the chemical to be sensed as previously described with respect to having all components on a single integrated circuit.

If the chemical sensor 34 is on a different die than the analog to digital converter 38, the analog signal has to pass from the sensor 34 on the first die 32 to the analog to digital converter 38 on the second die 36 in order for the data to be converted to the digital signal. This requires some type of outside connection between the first and second semiconductor dice 32, 36. In order to send an electrical signal on a separate wire, a larger signal may be needed to assure a high enough amplitude to be transmitted along the wire. This may require a larger sample of the chemical to be sensed. In addition, all electrical connections induce noise into the signal and an exposed wire is also susceptible to noise from multiple sources. Accordingly, such connections are very susceptible to noise from multiple sources. The signal must be substantially larger than the noise so as to have a high signal-to-noise ratio. If the signal has approximately the same amplitude as the noise in the system, then it is difficult or virtually impossible to separate the signal from the noise in properly converting the analog signal to a digital signal.

Having the chemical sensor 34 on the same semiconductor die 32 as the analog to digital converter 38, with each of them in the same integrated circuit, provides a number of advantages. A first advantage is that the pathway that the analog signal must travel before conversion is much shorter. In the case of the present invention, the signal path from the chemical sensor 34 to the analog to digital converter 38 is approximately the vertical height of the structure above the die 32, which is a very short signal path. Accordingly, the signal path is very short, usually in the range of 3,000 Å to 7,000 Å. A further benefit is that the signal path can be very low resistivity. For example, the electrical connections from the chemical sensor to the microcomputer can all be made in a highly conductive copper interconnect, or in some cases aluminum. Accordingly, the electrical connections from the chemical sensor 34 to the analog to digital converter 38 will be of a low resistivity metal and thus a very low amplitude signal is carried with very low resistance from the chemical sensor 34 to the microcontroller 38. A yet further advantage is that the signal layers inside of the semiconductor die are not as susceptible to noise as signal paths which must leave the die. Within the semiconductor die, the electrical connections are made by deposited layers of metal over insulators, and thus there is little chance for noise to affect the interconnection points. Because the analog to digital converter 38 and the chemical sensor 34 of FIG. 10 are formed on the same die, attenuation of the analog signal is reduced, and the signal to noise ratio is increased. This allows for a more accurate conversion of the analog signal to the digital signal. Once the analog signal has been converted to the digital signal the digital signal is substantially immune to noise and can be more easily output to the microcontroller 42 on the second semiconductor die 36 without introducing errors or inaccuracy into the digital signal. With a more accurate digital signal the microcontroller 42 can compute a more accurate value of the concentration of the selected chemical.

Having a chemical sensor 34 and the analog to digital converter 38 on the same die increases sensitivity of the device with very small samples of the chemical to be sensed. As one example, the sensing of blood glucose today for a diabetes test usually requires a droplet of blood of a size in excess of one ml. With the present chemical sensor 34 on the same die 32 as the analog-to-digital converter 38, a picoliter of blood, which is nothing more than a small fleck of blood, is acceptable for sampling the blood glucose. Similarly, very small quantities of other chemicals can be sensed, such as a few atoms of carbon monoxide, very small concentrations of lead in the water, and other chemicals having a concentration lower than parts per trillion. For example, chemicals having concentrations in the environment in the range of one quadrillion or one quintillion can be sensed because of the immunity to noise once the analog signal has been converted to the digital signal. The circuitry and process for forming an analog to digital converter 38 is far less complex than the circuitry and process for forming a microcontroller 42. Manufacturing an analog to digital converter 38 requires far fewer process steps than manufacturing a microcontroller 42. An analog to digital converter 38 may be formed using far fewer masks than a microcontroller 42. Fewer masks means far fewer process steps including time consuming and expensive mask alignment steps. Because the analog to digital converter 38 is far less complex than the circuitry for forming a microcontroller 42, a first semiconductor die 32 including a chemical sensor 34 and an analog to digital converter 38 can still be manufactured relatively inexpensively.

A first semiconductor die 32 including a chemical sensor 34 and an analog to digital converter 38 is an inexpensive part in a chemical detection system 30. This allows the first semiconductor die 32 to be a replaceable component of the system 30 without being prohibitively expensive. This is particularly advantageous for systems in which the chemical sensor 34 must be replaced after each use. After each use of the system 30, the first semiconductor die 32 can be inexpensively replaced and the system 30 can be reused.

The circuitry of a microcontroller 42 is typically much more complex than the circuitry in an analog to digital converter 38. Thus, the first semiconductor die 32 having both the chemical sensor 34 and the analog to digital converter 38 can still be manufactured relatively cheaply. The first semiconductor die 32 can be a replaceable component of the system 30 as described above.

Figure 11:
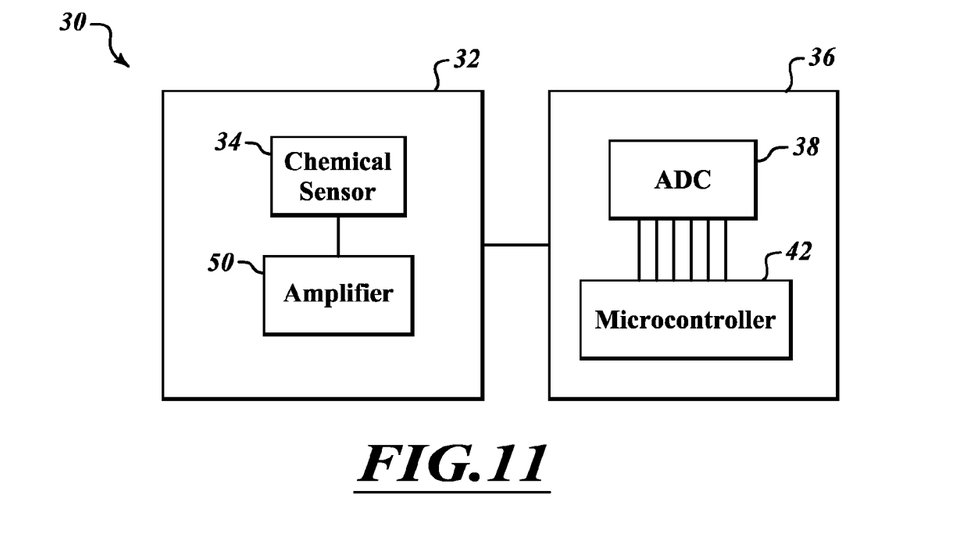
FIG. 11 is a block diagram of a two die chemical detection system according to a further embodiment.

FIG. 11 illustrates a chemical detection system 30 according to one embodiment. The amplifier 50 and the chemical sensor 34 are formed in the first semiconductor die 32. The analog to digital converter 38 and microcontroller 42 are formed in the second semiconductor die 36. The components function as described previously.

Figure 12:
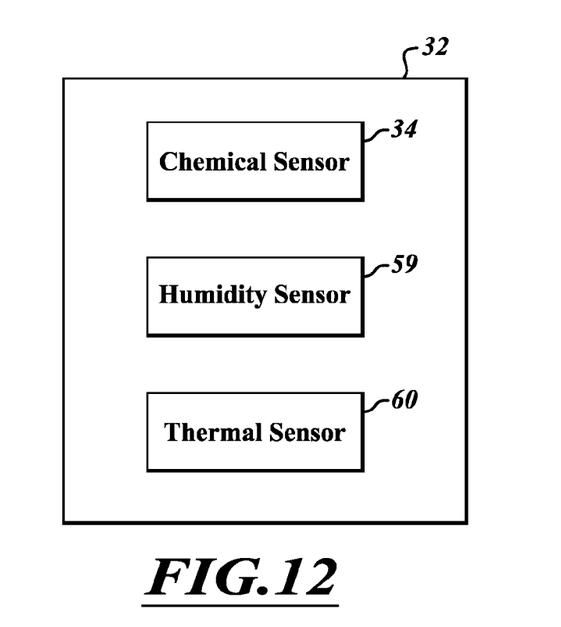
FIG. 12 is a block diagram of the first semiconductor die according to one embodiment.

FIG. 12 illustrates the first semiconductor die 32 according to one embodiment. The first semiconductor die 32 includes a chemical sensor 34, a humidity sensor 59, and a thermal sensor 60. The analog signal output by the chemical sensor 34 can be influenced not only by the concentration of the selected chemical, but also by the humidity and temperature. It thus can be beneficial to have a measurement of the humidity and temperature in order to more accurately estimate or compute the value of the concentration of the selected chemical. In such an embodiment the microcontroller 42 will receive not only the digital signal from the analog to digital converter 38, but also a humidity and temperature signal. The microcontroller 42 can thus include humidity and temperature data when estimating or computing the value of the concentration of the selected chemical.

The microcontroller 42 may reference calibration curves or tables stored in memory and compare values stored in memory to the values of the digital signals output by the analog-to-digital converter 38. By comparing the values of the digital humidity signal, the digital chemical signal, and the digital thermal signal to the values stored in memory, the microcontroller 42 can estimate or compute a more accurate value of the concentration of the selected chemical. The conversion table may have different values for the conversion depending on the temperature of the sensor, the humidity of the sensor, and other factors. Thus, the conversion table may include a plurality of separate tables, one for each temperature or temperature range, and again, depending on the selected chemical to be sensed and whether or not the sensing varies according to temperature. There are a number of well-known techniques for converting an analog signal representative of the presence of a selected chemical to a data value indicative of the concentration of that selected chemical.

Figure 13:
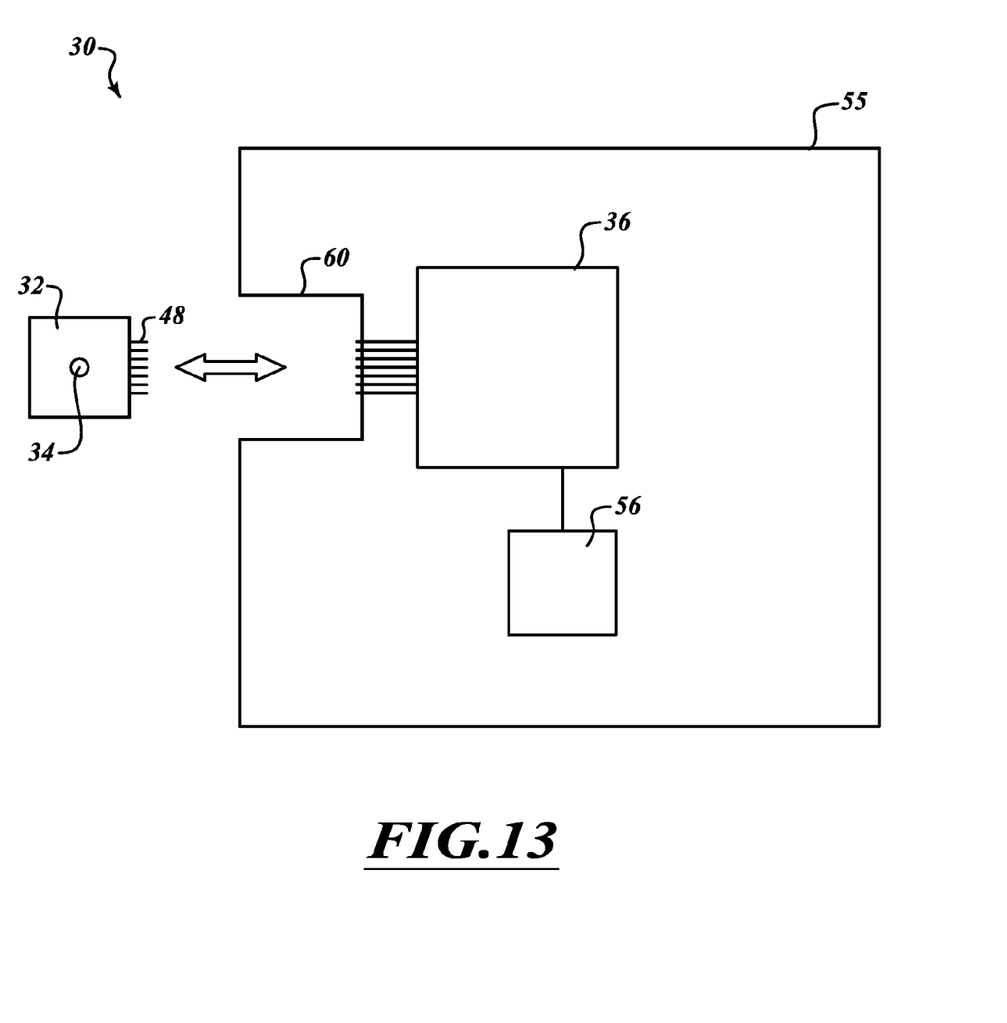
FIG. 13 is a chemical detection system according to one embodiment.

FIG. 13 illustrates a chemical detection system 30 according to one embodiment. The system 30 includes a casing 55. The casing 55 houses second semiconductor die 36. The second semiconductor die 36 includes at least a microcontroller 42 (not shown). A battery 56 is coupled to the second semiconductor die 36 and supplies power to the second semiconductor die 36. The casing 55 includes a die receiving slot 60 for receiving the first semiconductor die 32. The first semiconductor die 32 includes a chemical sensor 34 and electrical connections 48 for interfacing with the die receiving slot 60. The die receiving slot 60 is designed to enable easy installation and removal of the first semiconductor die 32.

In one embodiment the analog to digital converter is also formed in the second semiconductor die 36. In one embodiment, the system 30 is a multiple use chemical detection system. Because the first semiconductor die 32 can be easily installed and easily removed from the system 30, the system 30 can be used in an inexpensive manner to perform multiple chemical detections. For example, in one embodiment, the chemical detection system 30 is an exhaust detection system for an automobile.

In one embodiment the casing 55 is placed in or near the tailpipe of the automobile. A first semiconductor die 32 having a chemical sensor 34 designed to detect a selected chemical can be installed in the casing 55 by attaching the first semiconductor die 32 to the die receiving slot 60. A test can then be performed in which the chemical sensor 34 detects the selected chemical. The chemical sensor 34 outputs an analog signal to the digital to analog converter 38 as described previously. The digital to analog converter 38 then converts the analog signal to a digital signal. The digital to analog converter 38 then outputs the digital signal to the microcontroller 42. The microcontroller 42 then computes or estimates a value of the concentration of the selected chemical in the exhaust of the automobile. In one embodiment the chemical sensor 34 is designed to detect carbon dioxide in the exhaust. In one embodiment the chemical sensor 34 is designed to detect other particulates in the exhaust of the automobile.

After the microcontroller 42 estimates or computes the value of the concentration of the selected chemical in the exhaust, the microcontroller 42 can output the value to a display 50 (not shown). The display 50 can be attached to the casing 55 or the display can be on a remote computer screen. The display 50 may take many forms. For example, the display 50 can be a screen, a paper printout of the value of the concentration of the selected chemical, or any other suitable structure or method for displaying the value of the concentration. After the test has been performed, the first semiconductor die 32 can be removed from the casing 55 and another semiconductor die 32 having a chemical sensor 34 can be installed in the casing 55. The newly installed semiconductor die 32 may contain a chemical sensor 34 that is designed to detect the presence of a different selected chemical. In this way, the system 30 may be used to perform multiple successive chemical tests. Because each first semiconductor die 32 does not contain a microcontroller 42 or other complex circuitry, each semiconductor die 32 is relatively inexpensive to manufacture. This enables the inexpensive repeated testing using a single chemical detection system 30 by replacing the first semiconductor die 32 after each test.

In one embodiment the casing 55 contains a plurality of die receiving slots 60 so that a plurality of first semiconductor dies 32 each containing a respective chemical sensor 34 can be installed. The respective chemical sensors 34 are each designed to detect a respective selected chemical. In this way, multiple chemicals can be detected in a single testing session. The microcontroller 42 formed in the second semiconductor die 36 can be configured to interface with multiple die receiving slots 60 each containing a separate semiconductor die 32. The system 30 can then be used to simultaneously test for multiple chemicals in the exhaust of the automobile. The second semiconductor die 36 may contain a single analog to digital converter 38 or multiple analog to digital converters 38. The single analog to digital converter 38 or the multiple analog to digital converters 38 can process the analog signals from the chemical sensors 34 of the respective first semiconductor dies.

As described previously, the analog to digital converter can be formed either in the second semiconductor die 36 or each first semiconductor die 32 may contain a separate analog to digital converter 38. Because the analog to digital converter 38 is a relatively simple circuit, it can be formed inexpensively in the first semiconductor die 32. If the first semiconductor die 32 contains an analog to digital converter 38, the first semiconductor die 32 may still be manufactured relatively inexpensively. In this way, a chemical detection system 30 which utilizes replaceable first semiconductor dies 32 each containing a chemical sensor 34 can be an inexpensive way to make multiple chemical tests.

In one embodiment each first semiconductor die 32 includes a plurality of separate chemical sensors 34 each configured to detect a different respective selected chemical. This allows a chemical detection system 30 to simultaneously detect multiple selected chemicals while utilizing a single first semiconductor die 32 installed in the die receiving slot 60.

The chemical detection system 30 can be other than a system to detect chemicals in the exhaust of an automobile. As described previously, such a system can be implemented in a variety of ways, including medical tests such as blood glucose test systems, cancer cell test systems, water contaminant test systems, air pollution test systems, radon detection systems, and any other suitable chemical detection system.

Figure 14:
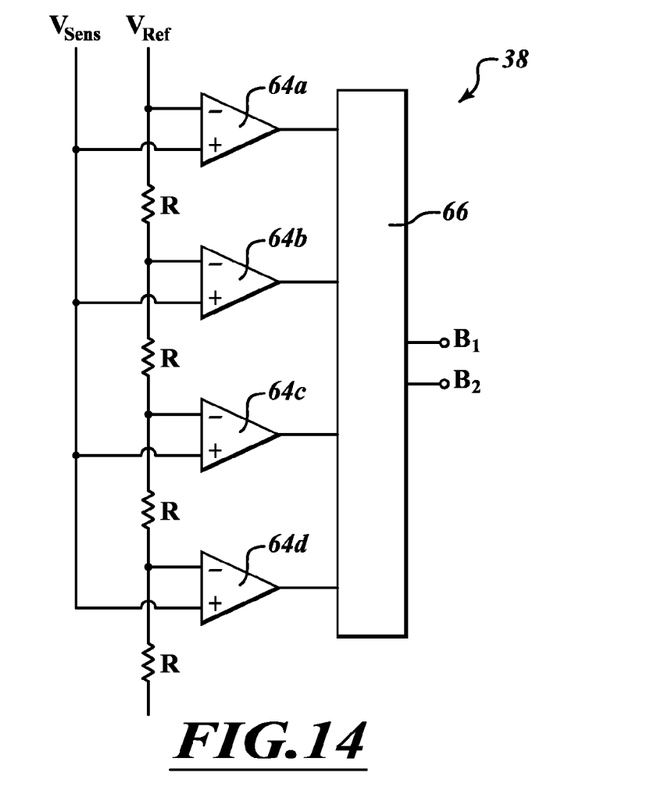
FIG. 14 is a schematic diagram of an analog to digital converter according to one embodiment.

FIG. 14 is an analog to digital converter according to one embodiment. The analog to digital converter includes comparators 64a, 64b, 64c, and 64d. The analog to digital converter 38 further includes four resistors R connected in series. Each comparator 64a-d is connected to the analog signal Vsense on its non-inverting input. Each comparator The analog-to-digital converter 38 includes four comparators 64a, 64b, 64c, and 64d each receiving the midpoint voltage on a respective non-inverting node. A plurality of resistors R of equal value is connected in series between a reference voltage Vsense and $V_L$. The inverting inputs of the comparators 64a, 64b, 64c, and 64d are each connected to a respective node on the series chain of resistors R. The outputs of the comparators are each connected to a digital output encoder 66. The digital output encoder has two outputs B1, B2 each representing a respective bit of the digital output.

Each comparator 64a, 64b, 64c, 64d of the analog-to-digital converter 38 compares the analog voltage Vsense to a respective reference voltage. The respective reference voltages are divisions of the primary reference voltage Vref. The chain of resistors R thus acts as a voltage divider to provide a plurality of reference voltages. Each comparator 64a, 64b, 64c, 64d will output a high or low value according to the individual comparisons. The digital outputs B1 and B2 are determined by the comparisons. In particular the digital output encoder includes a plurality of logic gates configured to receive as four inputs the outputs of the comparators 64a, 64b, 64c, and 64d and to output two binary outputs B1 and B2 accordingly. The outputs B1, B2 can combine to make binary values 00, 01, 10, or 11.

The outputs B1 and B2 are read by the control circuitry of the microcontroller 42 and compared to values in memory. The analog-to-digital converter 24 of FIG. 13 illustrates only a two-bit analog-to-digital converter. In practice the analog-to-digital converter 38 may more than two bits, for example an 8 or 16 bit analog-to-digital converter. The threshold differences can be selected by selecting appropriate values of the resistors R connected in series. Many variations are possible as will be apparent to those of skill in the art in light of the present disclosure. All such embodiments fall within the scope of this disclosure.

Figure 15:
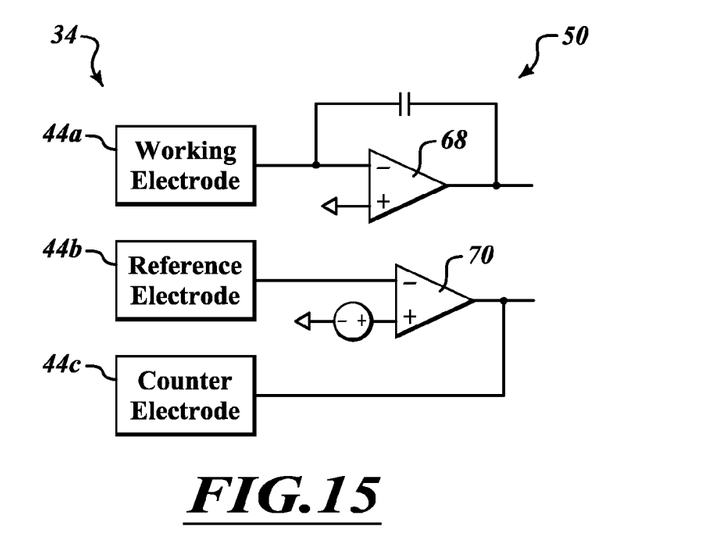
FIG. 15 is a schematic diagram of potentiostat and a chemical sensor according to one embodiment.

FIG. 15 illustrates a potentiostat according to one embodiment. The potentiostat 50 has a current integrator 68 and a control amplifier 70. FIG. 13 illustrates electrodes 44a, 44b, and 44c of the chemical sensor 34. The working electrode 44a is coupled to the inverting input of the current integrator. The inverting input of the control amplifier is connected to the reference electrode 44b of the chemical sensor 34. The output of the control amplifier 70 is coupled to the counter electrode 44c of the chemical sensor. The current integrator 68 outputs an analog signal representative of the concentration of the selected chemical. The control amplifier 70 ensures that the voltage on electrodes 44a, 44b is held at a selected value.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device comprising:
    a support structure;
    a die connection slot in the support structure;
    a first semiconductor die coupled to the die connection slot, the die connection slot configured to enable easy removal and installation of the first semiconductor die in the die connection slot;
    a chemical sensor located in the first semiconductor die, the chemical sensor being configured to output an analog signal indicative of a presence of a selected chemical;
    a second semiconductor die positioned in the support structure and coupled to the first semiconductor die;
    an analog to digital converter formed in the second semiconductor die, the analog to digital converter being configured to receive the analog signal and to convert the analog signal to a digital signal;

a third semiconductor die positioned in the support structure and coupled to the second semiconductor die; and a microcontroller formed in the third semiconductor die, the microcontroller configured to receive the digital signal from the analog to digital converter and to compute a value of a concentration of the selected chemical based on the digital signal.

2. The device of claim 1 wherein the second semiconductor die includes a signal amplifier configured to amplify the analog signal and to output the analog signal to the analog to digital converter.

3. The device of claim 2 wherein the signal amplifier is a potentiostat.

4. The device of claim 1 wherein the first semiconductor die includes a humidity sensor configured to output a humidity signal indicative of humidity.

5. The device of claim 4 wherein the microcontroller is configured to estimate the concentration of the selected chemical based in part on the humidity signal.

6. The device of claim 1 further comprising a display coupled to the microcontroller and configured to display the value of the concentration of the selected chemical.

7. A system comprising:
a first semiconductor die;
a chemical sensor formed in the first semiconductor die, the chemical sensor configured to output an analog signal indicative of a presence of the selected chemical;
an analog to digital converter coupled to the chemical sensor and configured to convert the analog signal to a digital signal;
a second semiconductor die coupled to the first semiconductor die; and
a microcontroller formed in the second semiconductor die, the microcontroller configured to receive the digital signal and estimate a concentration of the chemical based on the digital signal.

8. The system of claim 7 wherein the analog to digital converter is formed in the first semiconductor die.

9. The system of claim 7 wherein the analog to digital converter is formed in the second semiconductor die.

10. The system of claim 7 comprising an amplifier coupled to the chemical sensor and the analog to digital converter, the amplifier configured to amplify the analog signal and to output the analog signal to the analog to digital converter.

11. The system of claim 10 wherein the amplifier is a potentiostat.

12. The system of claim 10 wherein the amplifier is formed in the first semiconductor die.

13. The system of claim 10 wherein the amplifier is formed in the second semiconductor die.

* * * * *